United States Patent

Biedermann et al.

Patent Number: 5,609,637
Date of Patent: Mar. 11, 1997

[54] SPACE KEEPER, IN PARTICULAR FOR AN INTERVERTEBRAL DISK

[76] Inventors: Lutz Biedermann, Am Schäfersteig 8, D-78048 VS-Villingen; Jürgen Harms, Maximilianstr. 5, D-76133 Karlsruhe, both of Germany

[21] Appl. No.: 632,327

[22] Filed: Apr. 17, 1996

Related U.S. Application Data

[63] Continuation of Ser. No. 367,335, filed as PCT/EP94/02021 Jun. 21, 1994 published as WO95/01763 Jan. 19, 1995, abandoned.

[30] Foreign Application Priority Data

Jul. 9, 1993 [DE] Germany ............ 43 23 034.2

[51] Int. Cl.$^6$ .................................................. A61F 2/44
[52] U.S. Cl. ........................................................ 623/17
[58] Field of Search .......................... 623/17; 606/69, 606/61

[56] References Cited

U.S. PATENT DOCUMENTS

| | | | |
|---|---|---|---|
| 4,820,305 | 4/1989 | Harms et al. | 623/16 |
| 4,904,261 | 2/1990 | Dove et al. | 623/17 |
| 5,405,391 | 4/1995 | Henderson et al. | 623/17 |
| 5,425,772 | 6/1995 | Brantigan | 623/17 |
| 5,458,638 | 10/1995 | Kuslich et al. | 623/17 |

FOREIGN PATENT DOCUMENTS

| | | |
|---|---|---|
| 0268115 | 5/1988 | European Pat. Off. |
| 0538183 | 4/1993 | European Pat. Off. |
| 9216092 U | 1/1993 | Germany. |
| 1424826 | 9/1988 | U.S.S.R. ............ 606/61 |
| 1650114 | 5/1991 | U.S.S.R. ............ 606/61 |

Primary Examiner—David H. Willse
Attorney, Agent, or Firm—George W. Neuner

[57] ABSTRACT

A space keeper, in particular for substituting an intervertebral disk, is provided which comprises a cage-shaped wall (1) having a plurality of holes (4, 5) therein and a plurality of points (6) at both edges of the wall. In order to avoid the need for the operating person to keep different types on stock for corresponding different sections, the points (6) have severable portions (7) for adjusting the sectional form.

7 Claims, 2 Drawing Sheets

SPACE KEEPER, IN PARTICULAR FOR AN INTERVERTEBRAL DISK

This application is a continuation of application Ser. No. 08/367,335, filed as PCT/EP94/02021 Jun. 21, 1994 published as WO95/01763 Jan. 19, 1995, now abandoned.

A space keeper is known from EP B10 268 115. The space keeper described therein is intended in particular for substituting a vertebra. The two edges of the cage are parallel to each other.

It is the object of the invention to form a space keeper of the above-described kind in such a manner that it can be used in particular for substituting an intervertebral disk.

Further developments of the invention are defined in the dependent claims.

Further features and advantages of the invention will be evident from the description of an embodiment with reference to the Figures. In the Figures FIG. 1 is a side view of the space keeper;

Figure 1:
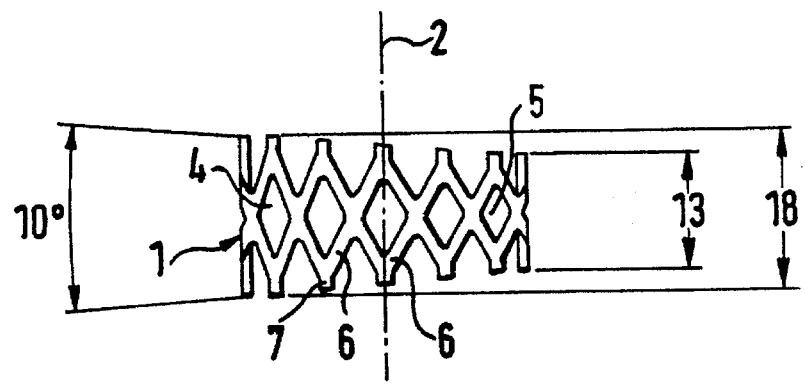

The space keeper has a cage-shaped wall 1. The cross-section of the hollow space defined by the cage is preferably of oval shape. According to modified embodiments this cross-section is reniform or approximately cylindrical, resp. In the manner shown in the Figures the wall 1 has diamond-shaped holes 3 having a long diagonal which extends parallel to the axis 2 of the space keeper. As shown in the Figures, the diamonds 4 on the one side have a maximum height and the diamonds 5 at the opposite side have a minimum height. The intermediate diamonds are formed to have a height which steadily decreases from the highest diamonds to the smallest diamonds. The ends of the diamonds at the upper end lower edges project upwards and downwards as points 6. As shown in the Figures each point 6 comprises a projecting portion 7 extending substantially parallel to the axis 2. The portions are of substantially uniform length. The different height of the diamonds results in a space keeper having two edges defining the point-shaped portions, the two edges including an angle so that the section of the space keeper is wedge-shaped. The wedge angle is preferably in a range of between 8° to 12° and in particular in the range of between 9° to 11° and according to a particularly preferred embodiment around 10°.

Figure 2:
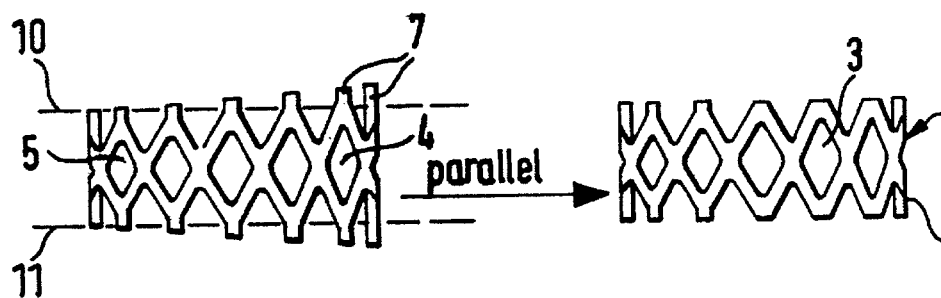
FIG. 2 is a side view of the space keeper with cutting lines and adjusted space keeper contour.
Figure 3:
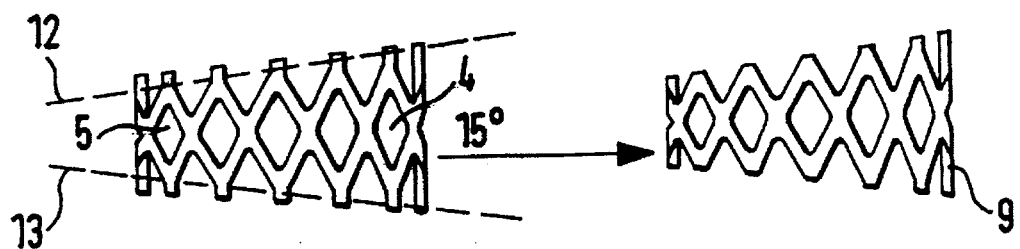
FIG. 3 shows the space keeper with cutting lines and a modified adjusted contour.

The length of the axially extending portions 7 is selected so that a space keeper 8 having parallel edges and therefore a rectangular section is obtained if, as shown in FIG. 2, in the region of the diamonds 4 having a maximum height the portions 7 are sheared off along the lines 10 and 11 and the portions of those diamonds which lie between the diamond 4 of maximum height and the diamond 5 of minimum height are partly cut off. With such a length of the portions 7 a space keeper 9 can be formed having a larger wedge angle than that of the original type, preferably in the range of between 14° to 16° and in particular at about 15°, if the portions at the diamond 5 having a minimum height are sheared off and the portions of the diamonds lying in between the diamond 4 of maximum height and the diamond 5 of minimum height are partly sheared off.

In particular titanium sheet material or a titanium tube, resp., or a body resorbing resin material is selected as a material for the space keepers.

Figure 4:
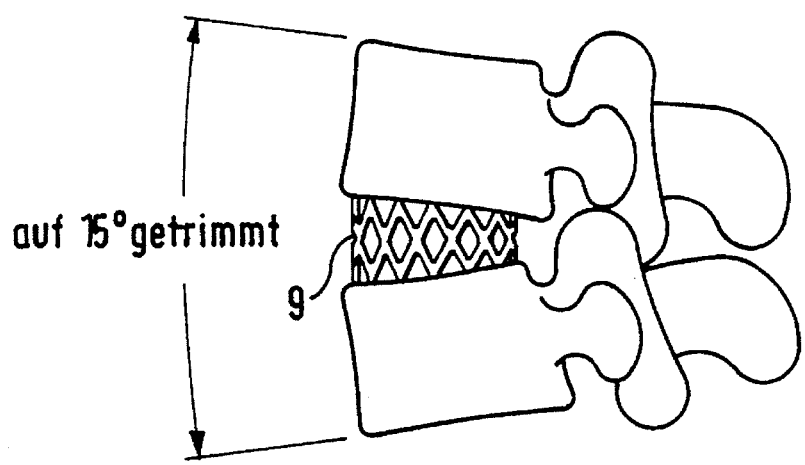
FIGS. 4 to 6 show space keepers of various shapes inserted between vertebrae.
Figure 5:
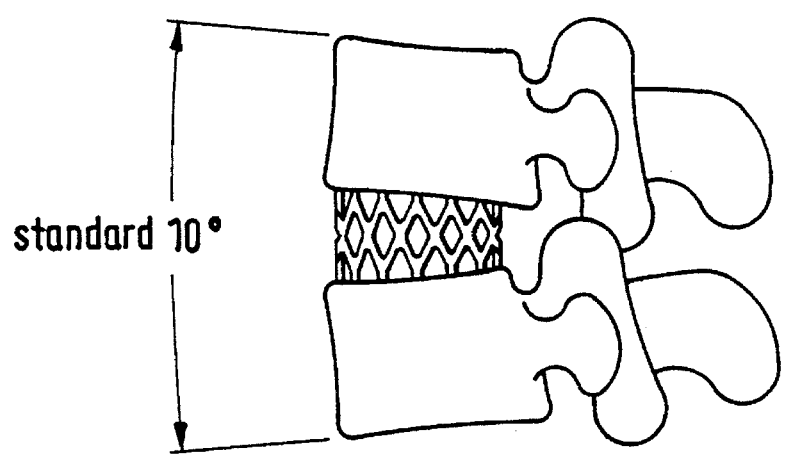
Figure 6:
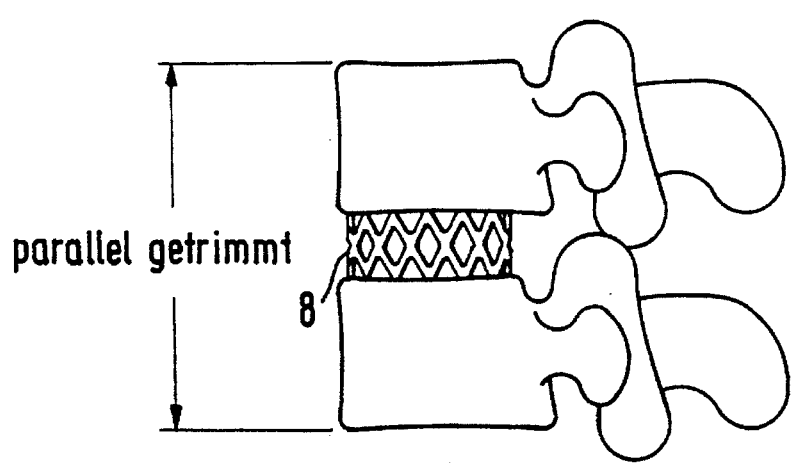

The desired shape 8 or 9, resp., of the above-described space keeper is obtained by an operating person by cutting off the points along the dotted cutting lines 10, 11 or 12, 13, resp. Thereupon the adjusted space keeper can be inserted between the vertebrae according to FIGS. 4 and 6, or in its original form according to FIG. 5.

The aforementioned design of the space keeper not only allows a simple adjustment to various wedge shapes of a space keeper for use in particular for the intervertebral disk, but also results in a considerably simplified store keeping, because the operating person needs to keep on stock only a single type of space keeper.

We claim:

1. A space keeper for replacing an intervertebral disk, the space keeper comprising:

a wall being closed around an axis defining a hollow body generally sized and shaped to replace said intervertebral disk, said wall having two opposite edges providing a bottom and a top surface of said body, a plurality of holes defined by said wall, said holes being disposed circumferentially around said wall and having a height in a direction parallel to said axis, said height decreasing from a maximum value at one side of said wall to a minimum value at an opposite side of said wall, a plurality of points provided at said edges, and severable projecting portions provided at said points for adjusting said shape by severing selected ones of said portions.

2. The space keeper of claim 1, wherein said top and bottom surfaces include an angle with respect to said axis whereby said body is wedge-shaped.

3. The space keeper of claim 2, wherein said angle is in the range of about 8° to about 12°.

4. The space keeper of claim 3, wherein said angle is in the range of about 9° to 11°.

5. The space keeper of claim 1, wherein said holes are formed as quadrangles or diamonds a diagonal of which extends in the direction of said axis.

6. The space keeper of claim 5, wherein said points are defined by ends of the quadrangles or the diamonds projecting upwards and downwards at said opposite edges, respectively.

7. The space keeper of claim 1, wherein said hollow body defined by said wall has a substantially oval cross-section perpendicular to said axis.

\* \* \* \* \*